United States Patent [19]

Jureidini

[11] Patent Number: 4,758,221
[45] Date of Patent: Jul. 19, 1988

[54] CATHETER WITH A TIP MANIPULATION FEATURE

[75] Inventor: Saadeh Jureidini, St. Louis County, Mo.

[73] Assignee: St. Louis University, St. Louis, Mo.

[21] Appl. No.: 768,202

[22] Filed: Feb. 18, 1986

[51] Int. Cl.$^4$ ............................................. A61M 37/00
[52] U.S. Cl. ........................................ 604/95; 604/98; 604/100; 604/96
[58] Field of Search ...................... 604/95, 96, 97, 98, 604/99, 100, 101, 102, 103; 128/344, 348.1

[56] References Cited

U.S. PATENT DOCUMENTS

| | | | |
|---|---|---|---|
| 3,119,392 | 1/1964 | Zeiss | 604/95 |
| 3,324,847 | 6/1967 | Zoumboulis | 604/96 |
| 3,605,725 | 9/1971 | Bentov | 604/95 |
| 4,003,382 | 1/1977 | Dyke | 604/103 |
| 4,245,624 | 1/1981 | Komiya | 604/95 |
| 4,543,090 | 9/1985 | McCoy | 604/95 |
| 4,586,923 | 5/1986 | Gould et al. | 604/95 |
| 4,665,925 | 5/1987 | Millar | 604/96 |

Primary Examiner—C. Fred Rosenbaum
Assistant Examiner—H. Macey
Attorney, Agent, or Firm—Senniger, Powers, Leavitt & Roedel

[57] ABSTRACT

A catheter with a tip manipulation feature, comprising an outer tube of flexible resilient material having a proximal end and a distal end terminating in a tip. The interior of the tube is divided into first and second lumens extending lengthwise of the tube, the first lumen being adapted for passage of fluid such as blood therethrough. A pull line extends lengthwise of the tube inside the second lumen and exits the second lumen through an opening in the tube wall proximal to the tip of the tube. From this opening the pull line extends along the tube wall on the outside of the tube in a direction toward the tip of the tube and is attached to the outside of the wall of the tube adjacent the tip of the tube whereby tensioning of the pull line bends the tip of the tube thereby to manipulate it into a desired position. The tip resiliently returns to its original unstressed shape when the tension on the pull line is released.

6 Claims, 2 Drawing Sheets

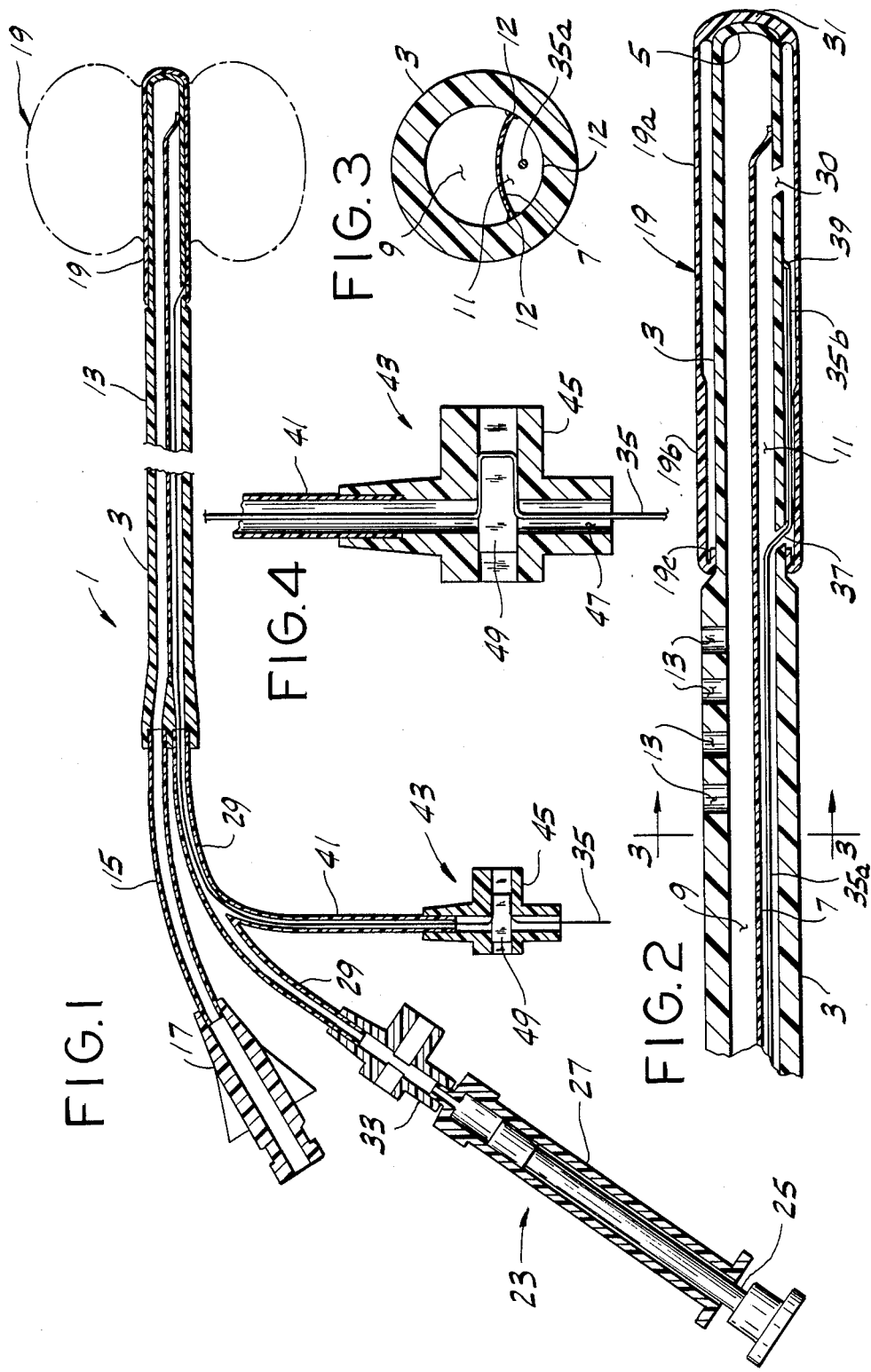

CATHETER WITH A TIP MANIPULATION FEATURE

BACKGROUND OF THE INVENTION

This invention relates generally to catheters and, more particularly, to a cardiovascular catheter having a unique tip manipulation feature for enabling the tip of the catheter to be directed in the desired direction to facilitate catheterization.

This invention is especially (albeit not exclusively) suited for use with balloon catheters, which are commonly used in cardiovascular catheterization. While various techniques have been used in an effort to manipulate a catheter to control the direction of tip movement during catheterization, such efforts have proven generally less than satisfactory. As a result, proper cardiovascular catheterization with only minimal stress to the patient is very difficult to accomplish, especially in cases involving unusual or abnormal origin and positions of the great vessels associated with cardiac dilatation, abnormal rotations, and congenital cardiac malformations.

SUMMARY OF THE INVENTION

Among the several objects of this invention may be noted the provision of a catheter with a tip manipulation feature whereby movement of the tip of the catheter may be closely controlled during catheterization to facilitate proper catheterization with minimal stress to the patient; the provision of a catheter wherein such feature is safe and easy to use; and the provision of a catheter wherein such feature is simple in design for inexpensive manufacture.

Generally, a catheter having a tip manipulation feature of this invention comprises an outer tube of flexible resilient material having a proximal end and a distal end terminating in a tip, the tube having a generally cylindric wall, means inside the outer tube defining first and second lumens extending lengthwise of the tube, the first lumen being adapted for passage of fluid such as blood therethrough, and a pull line having a first reach extending lengthwise of the tube inside the second lumen and a second reach exiting the second lumen through an opening in the tube wall proximal to the tip of the tube. The second reach of the pull line extends from said opening along the tube wall on the outside of the tube in a direction toward the tip of the tube and is attached to the outside of the wall of the tube adjacent the tip of the tube whereby tensioning of said first reach of the pull line is adapted to bend the tip of the tube thereby to manipulate it into a desired position, said tip being adapted resiliently to return to its original unstressed shape when the tension on the pull line is released.

Other objects and features will be in part apparent and in part pointed out hereinafter.

BRIEF DESCRIPTION OF THE DRAWINGS

FIG. 1 is a view illustrating a catheter having a tip manipulation feature of this invention;

FIG. 2 is an enlarged portion of FIG. 1 showing the tip area of the catheter;

FIG. 3 is an enlarged section taken on line 3—3 of FIG. 2;

FIG. 4 is an enlarged portion of FIG. 1 showing valve means;

Corresponding reference characters indicate corresponding parts throughout the several views of the drawings.

DESCRIPTION OF THE PREFERRED EMBODIMENT

Figure 5:
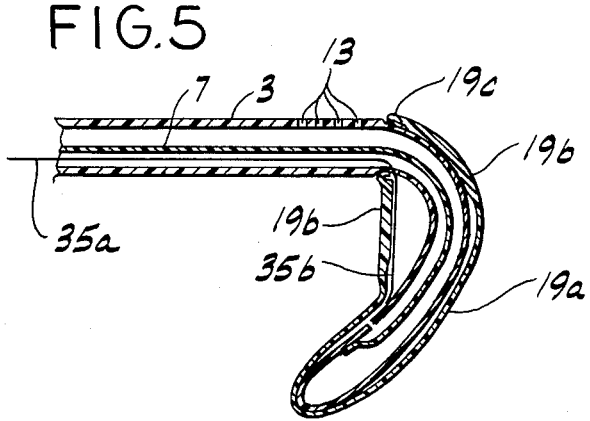
FIG. 5 is a view illustrating how the tip of the catheter is manipulated.
Figure 6:
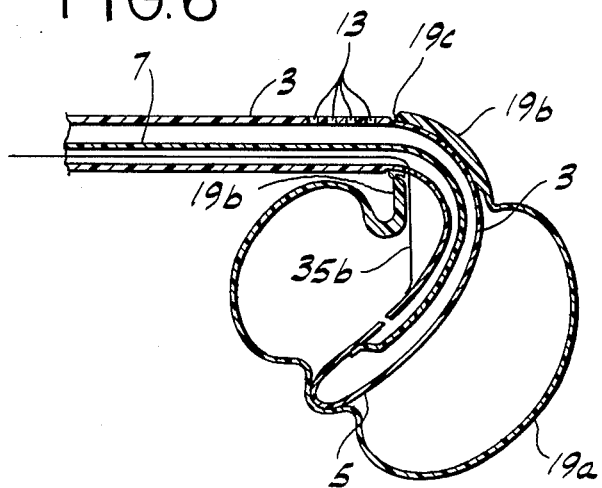
FIG. 6 is a view similar to FIG. 5 showing a balloon at the tip of the catheter inflated.

Referring now to the drawings, particularly FIGS. 1 and 2, a catheter having a tip manipulation feature of this invention is designated in its entirety by the reference numeral 1. As illustrated, the catheter is a balloon catheter of the type commonly used in cardiovascular catheterization of infants, although it is contemplated that the tip manipulation feature hereinbelow described is also suitable for catheters of different types.

More particularly, the catheter comprises an outer tube 3 having a generally cylindric wall of soft flexible resilient material, such as polyethylene, polyurethane, nylon or other suitable material known to those skilled in the art. The tube 3 has a proximal end (left end as viewed in FIG. 1) and a distal (right) end terminating in a closed tip 5 which is rounded. Means comprising an inner partition 7 of resilient material (e.g., the same material as outer tube 3) extending lengthwise of the outer tube on the inside thereof divides the interior of the outer tube into first and second lumens, indicated at 9 and 11, respectively, extending lengthwise of the catheter. The inner partition 7 is bonded at 12 to the outer tube 3 to secure the partition in fixed position with respect to the outer tube. A series of side holes, each designated 13, in the wall of the outer tube spaced proximally of its tip 5 constitute an inlet communicating with lumen 9 for flow of fluid (e.g., blood) into the first lumen. A smaller tube 15 is attached to the proximal end of the outer tube 3 and communicates with lumen 9. This tube 15 is secured at its distal (left) end to a fitting 17 which is adapted for connection to a pressure transducer, for example, (not shown) for measuring intravascular pressures.

As noted above, catheter 1 is a balloon catheter having an inflatable bag or balloon generally indicated at 19 at its distal end. The balloon is of resilient material and has an inflatable portion 19a, an uninflatable neck portion 19b having a wall thickness greater than that of the inflatable portion 19a, and a mouth 19c secured in sealing engagement around the outer tube 3 at a location spaced proximally of the tip 5 of the tube. The uninflatable portion of the balloon acts to help straighten the catheter by exerting pressure on the pull-line to recoil when tension on the pull line is discontinued. As shown best in FIG. 2, the distal portion of the outer tube 3 has a reduced wall thickness to accommodate the thickness of the balloon wall at its neck 19b, the result being that the outside diameter of the catheter is generally uniform along the entire length of the outer tube when the balloon is deflated.

The balloon is adapted to be inflated by means of a syringe generally indicated at 23 comrising a plunger 25 slidable in a barrel 27 for introducing a suitable gas (e.g., carbon dioxide) into a second smaller tube 29 attached at its distal end to the proximal end of the outer tube 3 and communicating with lumen 11 for flow of gas therethrough. The gas exits lumen 11 into the interior of the balloon 19 through an outlet hole 30 in the wall of the outer tube adjacent the tip of the tube. The balloon is suitably affixed to the tip 5 of the outer tube 3, as indicated at 31, so that when inflated, the inflatable portion 19a of the balloon expands laterally outwardly from the outer tube. A stopcock 33 immediately downstream from the syringe 23 may be opened and closed to control the flow of gas to and from the balloon.

The tip manipulation feature of this invention comprises a small-diameter pull line 35 of suitably strong material (e.g., 4-0 silk or nylon) having a first reach 35a extending lengthwise of the catheter inside the gas lumen 11 and a second reach 35b exiting the gas lumen through an exit opening 37 in the wall of the outer tube 3 spaced proximally of the tip 5 of the tube and distally of the location where the mouth of the balloon 19 is sealed against the wall of the tube. Reach 35b of the pull line extends from the exit opening 37 along the outside of the wall of the tube in a direction toward the tip 5 and is attached at 39 to the wall of the tube on the outside of the tube adjacent the tip, the entire reach 35b thus being disposed inside the balloon.

As illustrated in FIG. 1, the pull line 35 extends proximally from the outer tube 3 through smaller tube 29 and thence through a branch tube 41 branching off tube 7 to a stopcock generally designated 43 (constituting valve means). This stopcock comprises a valve body 45 having a passage 47 therethrough and a valve closure member 49 slidable in the valve body in a direction generally perpendicular to passage 47 between an open position (not shown) and a closed position (FIG. 4) in which it blocks the passage. The pull line extends through passage 47 and is sufficiently small in diameter to permit movement of the closure member 49 to its closed position wherein the line is caught between the closure member and the valve body. The proximal end of the pull line projects out of passage 47 so that it may be grasped.

The arrangement is such that tensioning of the pull line 35, as by pulling it by hand when stopcock 43 is open, bends the tip 5 of the outer tube to manipulate it in a desired direction, as illustrated in FIG. 5, the amount of bend being controlled by the extent to which the pull line is drawn in the proximal direction (i.e., toward the left as viewed in the drawings). It will be noted that when the pull line is tensioned to bend the tip 5, reach 35b of the line moves against the bias of the neck portion 19b of the balloon to assume a position in which it and the neck portion 19b are spaced from the wall of the outer tube 3. The fact that this reach of the line is contained entirely within the balloon eliminates the possibility of the line damaging adjacent body tissue. Manipulation of the tip 5 by tensioning the pull line 35 is performed while the stopcock 43 is open prior to inflation of the balloon 19. After the catheter has been maneuvered to the desired position the stopcock 43 may be closed by moving the valve closure member 49 to the position illustrated in FIG. 3 wherein the line is held by the closure member against the wall of the valve body 45 thereby to hold the line to maintain the tip in the desired position. The stopcock 33 may then be opened and the balloon inflated.

To return the tip 5 of the catheter to its straightened configuration, the stopcock 43 is opened and the tension on pull line 35 released, whereupon the resiliency of the inner and outer tubes 3, 7 and the neck portion 19b causes the catheter to straighten.

Figure 7:
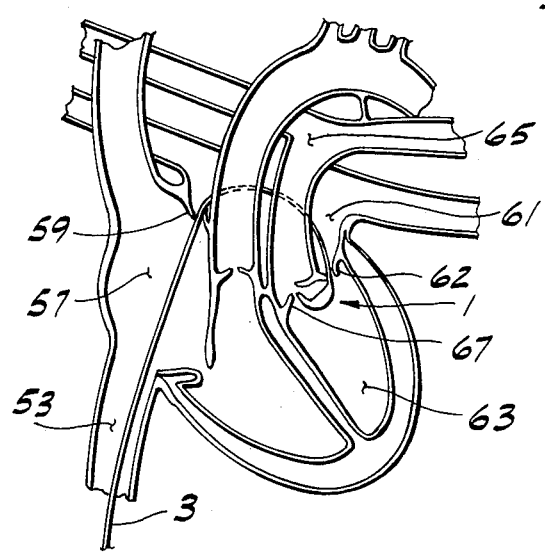
FIG. 7 is a view illustrating a cardiovascular catheterization operation using a catheter with the tip manipulation feature of this invention.

FIG. 7 illustrates the use of catheter 1 in a cardiovascular catheterization operation involving entry of the pulmonary artery where there is a D-transposition of the great arteries. With the balloon 19 deflated, stopcock 33 closed and stopcock 43 open, the catheter is inserted through the femoral vein (not shown) into the inferior vena cava 55 and thence to the right atrium 57, as detected by fluoroscopic examination. From the right atrium the catheter is advanced through a patent (open) foramen ovale 59 to the left atrium 61 and from there through the mitral valve 62 to the left ventricle 63. The tip of the catheter is then bent by tensioning the pull line 35 to form a loop of proper configuration which allows quick and safe entry of the catheter into the pulmonary artery 65 via the pulmonary valve 67. Subsequently stopcock 43 may be closed, stopcock 33 opened, and the balloon 19 inflated to facilitate entry of the catheter according to the flow directed catheter principle.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A catheter with a manipulation feature, comprising an outer tube of flexible resilient material having a proximal end and a distal end terminating in a tip, said tube having a generally cylindric wall, means inside the outer tube defining first and second lumens in the outer tube extending lengthwise of the tube, the first lumen being adapted for passage of fluid such as blood therethrough, and a pull line having a first reach extending lengthwise of the tube inside said second lumen and unattrorized thereto, and a second reach exiting the second lumen through an opening in the tube wall proximal to the tip of the tube, said second reach of the pull line extending from said opening along the tube wall on the outside of the tube in a direction toward the tip of the tube and being attached to the outside of the wall of the tube adjacent the tip of the tube whereby tensioning of said first reach of the pull line is adapted to effect movement of the first reach relative to the outer tube thereby to bend the tip of the tube to manipulate it into a desired position, said tip being adapted resiliently to return to its original unstressed shape when the tension on said pull line is released.

2. A catheter as set forth in claim 1 wherein said catheter further comprises an inflatable balloon at the distal end of said outer tube, said balloon having a mouth in sealing engagement around the outer tube at a location proximal of said exit opening for said pull line whereby said second reach of the pull line is contained substantially entirely within the balloon.

3. A catheter as set forth in claim 1 wherein said means defining said first and second lumens comprises an internal partition extending lengthwise of the outer tube on the inside of the tube.

4. A catheter with a manipulation feature, comprising an outer tube of flexible resilient material having a proximal end and a distal end terminating in a tip, said tube having a generally cylindric wall, means inside the outer tube defining first and second lumens in the outer tube extending lengthwise of the tube, the first lumen being adapted for passage of fluid such as blood therethrough, and a pull line having a first reach extending lengthwise of the tube inside said second lumen and a second reach exiting the second lumen through an opening in the tube wall proximal to the tip of the tube, said second reach of the pull line extending from said opening along the tube wall on the outside of the tube in a direction toward the tip of the tube and being attached to the outside of the wall of the tube adjacent the tip of the tube whereby tensioning of said first reach of the pull line is adapted to bend the tip of the tube thereby to manipulate it into a desired position, said tip being adapted resiliently to return to its original unstressed shape when the tension on said pull line is released; and an inflatable balloon at the distal end of said outer tube, said balloon having a mouth in sealing engagement around the outer tube at a location proximal of said exit opening for said pull line whereby said second reach of the pull line is contained substantially within the balloon; and an outlet opening in the outer tube providing communication between said second lumen and the interior of the balloon whereby gas from a suitable source may be introduced through the second lumen into the balloon to inflate it.

5. A catheter as set forth in claim 4 further comprising valve means movable between an open position and a closed position for blocking escape of gas from the balloon when the balloon is inflated, said pull line passing through said valve means and being adapted to be tensioned to bend the tip of the catheter when said valve means is open.

6. A catheter as set forth in claim 4 wherein said outlet opening is spaced distally of the outer tube from said exit opening for the pull line.

* * * * *